United States Patent [19]

Hayase et al.

[11] Patent Number: 4,681,874
[45] Date of Patent: Jul. 21, 1987

[54] THIAZINEPHOSPHONIC ACID DERIVATIVES

[75] Inventors: Yoshio Hayase; Mitsuhiro Ichinari, both of Mie; Junji Taguchi, Chiba; Takeo Ishiguro, Shiga; Toshio Takahashi, Hyogo, all of Japan

[73] Assignee: Shionogi & Co., Ltd., Osaka, Japan

[21] Appl. No.: 773,133

[22] Filed: Sep. 6, 1985

[30] Foreign Application Priority Data

Sep. 8, 1984 [JP] Japan ................... 59-188744

[51] Int. Cl.$^4$ .................. C07F 9/65; A01N 43/72; C07D 279/06
[52] U.S. Cl. ........................... 514/90; 544/54
[58] Field of Search ............. 544/54; 514/226, 90

[56] References Cited

U.S. PATENT DOCUMENTS

| | | | |
|---|---|---|---|
| 3,794,730 | 2/1974 | Szabo | 544/54 |
| 3,812,117 | 5/1974 | Gaughan | 544/54 |
| 4,460,579 | 7/1984 | Karanewsky | 544/54 |
| 4,531,002 | 7/1985 | Harris | 544/54 |

FOREIGN PATENT DOCUMENTS 3301347 7/1984 Fed. Rep. of Germany ........ 544/54

Primary Examiner—John M. Ford
Attorney, Agent, or Firm—Birch, Stewart, Kolasch and Birch

[57] ABSTRACT

Novel thiazinephosphonic acid derivatives (I):

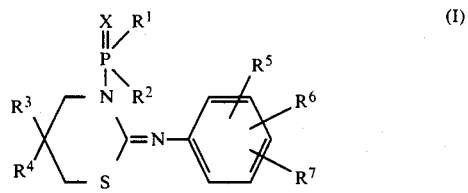

wherein $R^1$ and $R^2$ each is lower alkoxy, lower alkynyloxy, lower alkylthio, arylthio (e.g., monocyclic aromatic group), or lower alkylamino; $R^3$ and $R^4$ each is hydrogen or lower alkyl; $R^5$, $R^6$, and $R^7$ each is hydrogen, lower alyl, lower alkoxy, halogen, or trifluoromethyl; and X is oxygen or sulfur, are disclosed. A method for the production thereof, and pesticides comprising said compounds (I) are provided.

21 Claims, No Drawings

THIAZINEPHOSPHONIC ACID DERIVATIVES

BACKGROUND OF THE INVENTION

1. Field of the Invention

The present invention relates to novel thiazinephosphonic acid derivatives, production thereof, and pesticides comprising the thiazine phosphonic acid derivatives as an effective ingredient.

2. Prior Art

A lot of insecticides containing phosphorus atom are commercially available at present, while any insecticides having a thiazine ring are not known. A phosphonic acid diester bound to the nitrogen atom of a morphorinyl group is disclosed in JPN Unexamd. Pat Publn. No.49-101545, but no phosphorus compound having a thiazine ring is known.

BRIEF SUMMARY OF THE INVENTION

The present invention relates to a compound of the formula (I):

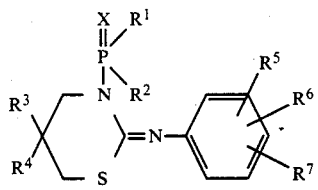
(I)

wherein $R^1$ and $R^2$ each is lower alkoxy, lower alkynyloxy, lower alkylthio, arylthio, or lower alkylamino; $R^3$ and $R^4$ each is hydrogen or lower alkyl; $R^5$, $R^6$, and $R^7$ each is hydrogen, lower alkyl, lower alkoxy, halogen, or trifluoromethyl; and X is oxygen or sulfur and production thereof; and it also relates to a pesticidal composition comprising one or more of said compounds and one or more carriers.

The compound (I) can be prepared by reacting a 2-phenylimino-3,4,5,6-tetrahydro-2H-1,3-thiazine (II) with a reactive phosphonic acid derivative (III).

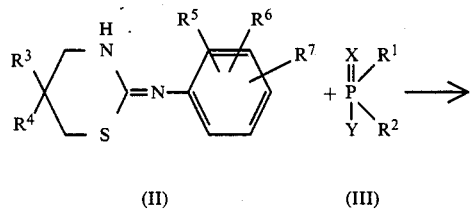

(II)    (III)

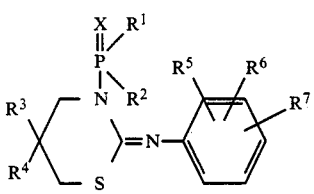

(I)

wherein $R^1$, $R^2$, $R^3$, $R^4$, $R^5$, $R^6$, $R^7$, and X each has the same meaning as defined above; and Y is a leaving group.

DETAILED DESCRIPTION OF THE INVENTION

The present invention relates to a compound of the formula (I):

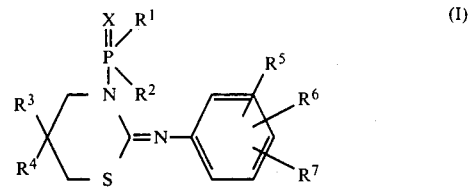
(I)

wherein $R^1$ and $R^2$ each is lower alkoxy, lower alkynyloxy, lower alkylthio, arylthio, or lower alkylamino; $R^3$ and $R^4$ each is hydrogen or lower alkyl; $R^5$, $R^6$, and $R^7$ each is hydrogen, lower alkyl, lower alkoxy, halogen, or trifluoromethyl; and X is oxygen or sulfur and it also relates to a pesticidal composition comprising one or more of said compounds (I) and one or more carriers.

Furthermore, the present invention also relates to a process for preparing the compound of the formula (I):

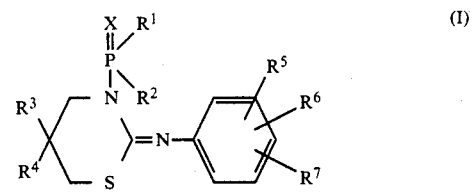
(I)

wherein $R^1$ and $R^2$ each is lower alkoxy, lower alkynyloxy, lower alkylthio, arylthio, or lower alkylamino; $R^3$ and $R^4$ each is hydrogen or lower alkyl; $R^5$, $R^6$, and $R^7$ each is hydrogen, lower alkyl, lower alkoxy, halogen, or trifluoromethyl; and X is oxygen or sulfur, which comprises reacting a compound of the formula (II):

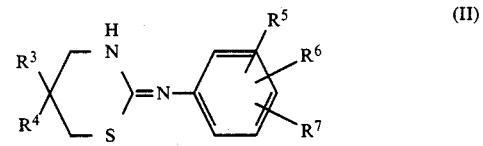
(II)

wherein $R^3$, $R^4$, $R^5$, $R^6$, and $R^7$ each has the same meaning as defined above, with a compound of the formula (III):

(III)

wherein $R^1$, $R^2$, and X each has the same meaning as defined above; and Y is a leaving group.

The present inventors have investigated various organic phosphorus pesticides and found that the 2-phenylimino-tetrahydro-1,3-thiazine-3-phosphonic acid esters (I) have potent pesticidal activities with low toxicities against human beings or animals. This invention is based on these findings.

The definitions in the above formulae will be explained in more detail as follows.

The group attached by the term "lower" in the definitions means a group having not more than 6 carbon atoms, especially not more than 5 carbon atoms, unless the term is particularly defined.

"The lower alkyl" means straight or branched chain saturated hydrocarbon residue, in particular $C_1-C_5$ alkyl. Examples of the lower alkyl are methyl, ethyl, propyl, isopropyl, butyl, isobutyl, sec-butyl, tert-butyl, pentyl, isopentyl, tert-pentyl, neo-pentyl, 1-methylbutyl, 1,2-dimethylpropyl, hexyl, and the like.

"The lower alkoxy" means a group formed from the above lower alkyl and a bivalent oxygen. Representatives of the lower alkoxy are $C_1-C_6$ alkoxy such as methoxy, ethoxy, propoxy, isopropoxy, butoxy, pentyloxy, hexyloxy, and the like.

"The alkynyloxy" includes $C_2-C_5$ alkynyloxy, for example, ethynyloxy, 2-propynyloxy, 3-butynyloxy, 4-pentynyloxy, etc.

"The alkylthio" means a group formed from the lower alkyl and a bivalent sulfur, especially $C_1-C_6$ alkylthio, for example, methylthio, ethylthio, propylthio, isopropylthio, butylthio, pentylthio, hexylthio, etc.

"The alkylamino" includes a group formed from the lower alkyl and an imino. Examples of the lower alkylamino are $C_1-C_6$ alkylamino such as methylamino, ethylamino, propylamino, isopropylamino, butylamino, pentylamino, hexylamino, and the like.

"The arylthio" is aryl, preferably a group formed from a monocyclic aryl or monocyclic aromatic group bound to a bivalent sulfur. The arylthio includes phenylthio, tolylthio, xylylthio, and the like.

"The halogen" includes fluorine, chlorine, bromine, iodine, and the like.

"The leaving group" means a group which can be easily eliminated during the reaction. Examples of the leaving group are acid residues such as chlorine, bromine iodine, and the like. The compound (I) can be prepared according to the following reaction sequence.

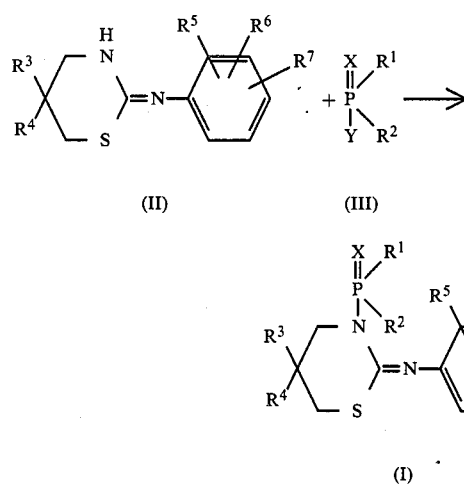

wherein $R^1$, $R^2$, $R^3$, $R^4$, $R^5$, $R^6$, $R^7$, and X each has the same meaning as defined above; and Y is a leaving group.

The reaction can be carried out even in the absence of a solvent, but preferably it proceeds in the presence of a solvent.

As the solvent, inert solvent such as aliphatic hydrocarbons (e.g., n-hexane, cyclohexane, etc.), aromatic hydrocarbons (e.g., benzene, toluene, xylene, etc.), ketones (e.g., acetone, methyl isobutyl ketone, etc.), ethers (e.g., diethyl ether, tetrahydrofurane, dioxane, etc.), halogenohydrocarbons (e.g., dichloromethane, chlorobenzene, etc.), and the like can be employed.

Preferably, this reaction is carried out in the presence of an acid-acceptor (a base).

The acid-acceptor includes organic base such as aliphatic tertiary amine (e.g., trimethylamine, triethylamine, tributylamine, etc.), aromatic amine (e.g., dimethylaniline, diethylaniline, etc.), and heterocyclic amine (e.g., pyridine, α-picoline, γ-picoline, etc.); and inorganic base such as sodium carbonate, potassium carbonate, and the like.

The reaction may be carried out at a temperature of $0°\sim100°$ C., preferably at a temperature of $20°\sim80°$ C. and it terminates within a period of 1 to 12 hours, preferably 2 to 8 hours.

The product can be isolated in a conventional manner for purification such as extraction, recrystallization, column-chromatography, or the like.

The starting material (II) may be prepared according to the following reaction sequence.

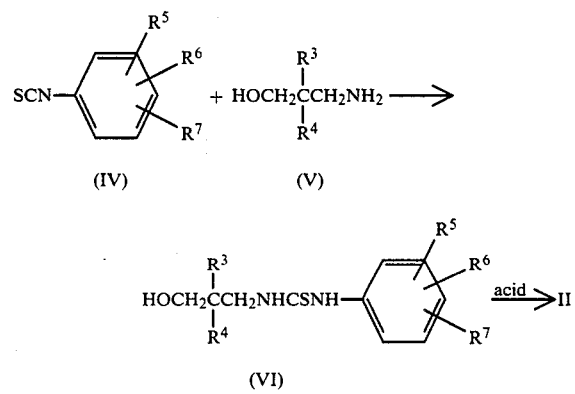

wherein $R^3$, $R^4$, $R^5$, $R^6$, and $R^7$ each has the same meaning as defined above.

The reaction of the compound (IV) with the compound (V) may be carried out in the absence or presence of a solvent with stirring at a temperature of $0°\sim60°$ C. for $10\sim60$ minutes. The solvent includes ether, benzene, and the like.

The compound (IV) is prepared from the corresponding amine in the same manner as described in, for example, J. Org. Chem. 29, 3098 (1964).

The compound (VI) can be converted into the compound (II) under reflux in the presence of an acid such as hydrochloric acid for 1 to 3 hours.

[Effect]

The compounds (I) have potent pesticidal activities against harmful plant-parasitic nematodes, insects belong to Orthoptera, Hemiptera, Lepidoptera, Diptera, Coleoptera (beetles), and mites. The compounds (I) can be employed by themselves or in a formulation such as powder, granules, wettable powder, emulsion, suspension, aerosol, flowable, and the like by mixing with appropriate solid or liquid carriers and adjuvants.

The formulations can be prepared in a conventional manner.

The solid carriers include vegetable powder (e.g., corn, soybean, wheat, wood), mineral powder (e.g., clay, bentonite, acid clay, vermiculite, talc, diatomaceous earth, pumice, active carbon), synthetic resin (e.g., vinyl chloride, polystyrene), and the like.

The liquid carriers include hydrocarbons (e.g., kerosene, solvent naphtha, toluene, xylene), alkanols (e.g., methanol, ethanol, ethylene glycol, polypropylene glycol), ethers (e.g., dioxane, cellosolve), ketones (e.g., methyl isobutyl ketone, cyclohexanone), halogenohydrocarbons (e.g., dichloroethane, trichloroethane), esters (e.g., dioctylphthalate), amides (e.g., dimethylformamide), nitriles (e.g., acetonitrile), fats and oils; and water.

As the adjuvant, surface active agents, wetting agents, sticking agents, thickeners, stabilizers, and the like may be employed. Examples of the adjuvants are anionic surface active agents (e.g., alkyl sulfonate, lignin sulfonate, alkylsulfate), nonionic surface active agents (e.g., alkylpolyoxyethylene ether, sorbitan ester, polyoxyethylene fatty acid ester, sucrose ester), water-soluble high-molecular compounds (e.g., casein, gelatin, CMC, PVA, gum arabic, alginic acid) can be used.

The compounds (I) are preferably used at a concentration of 0.1~99.9%, preferably 20~80% in the above formulation.

Furthermore, the compounds (I) can be used in combination with other insecticides, fungicides, herbicides, soil modifiers, fertilizers, and the like.

The application rate should be decided in consideration of the application method, application time, application place, objective insects, mites, or nematodes; or objective plants; generally the application rate is 1~500 g/10 are.

The present invention will be explained in more detail by the following Examples and the effect of the present invention will be confirmed by the following Experiments.

EXAMPLE 1

(Compound No. 25)

To a mixture of 5.64 g (25.6 mmol) of 2-phenylimino-5,5-dimethyl-3,4,5,6-tetrahydro-2H-1,3-thiazine, 2.85 g (28.2 mmol) of triethylamine, and 50 ml of benzene is dropwise added 5.29 g (25.6 mmol) of S-sec-butyl O-methyl monochlorothiolphosphonate with stirring at 10°~20° C. The mixture is allowed to react at 25°~30° C. for 6 hours; and the resulting triethylamine hydrochloride is removed by filtration. The benzene layer is washed with 3% hydrochloric acid, 3% aqueous sodium carbonate, and water; and then concentrated under reduced pressure to give 9.91 g of an oily material. The oily material is purified by silica-gel column chromatography (Wako gel C-300: registered trademark; solvent: n-hexane/acetone=10/1); and the fractions containing the objective compound are collected and the solvent is removed under reduced pressure to give 6.99 g (yield: 70.6%) of white crystalline S-sec-butyl O-methyl 2-phenylimino-5,5-dimethyl-3,4,5,6-tetrahydro-2H-1,3-thiazine-3-thiolphosphonate. m.p.: 41.0°~42.5° C.

EXAMPLE 2

(Compound No. 36)

To a mixture of 5.00 g (18.6 mmol) of 2-[(2-methyl-4-chlorophenyl)imino]-5,5-dimethyl-3,4,5,6-tetrahydro-2H-1,3-thiazine, 2.07 g (20.5 mmol) of triethylamine, and 50 ml of toluene is dropwise added 3.77 g (18.6 mmol) of S-sec-butyl O-methyl monochlorothiol-phosphonate at 10°~20° C. The mixture is stirred at 30°~35° C. for 4 hours. The resulting triethylamine hydrochloride is removed by filtration; the toluene layer is concentrated under reduced pressure to give 8.05 g of pale yellowish viscous oily material. The oily material is purified in the same manner as in Example 1 and the resultant transparent liquid is cooled to give 4.59 g (yield: 56.7%) of white crystalline S-sec-butyl O-methyl 2-[(2-methyl-4-chlorophenyl)imino]-5,5-dimethyl-3,4,5,6-tetrahydro-2H-1,3-thiazine-3-thiolphosphonate, m.p. 48.5°~49.5° C.

EXAMPLE 3

(Compound No. 2)

To a mixture of 1.00 g (5.20 mmol) of 2-phenylimino-3,4,5,6-tetrahydro-2H-1,3-thiazine, 0.58 g (5.72 mmol) of triethylamine, and 10 ml of toluene is dropwise added 1.14 g (5.20 mmol) of O-ethyl S-n-propyl monochlorodithiophosphonate with stirring at 10°~20° C. The mixture is stirred at 25°~30° C. for 4 hours. The resulting triethylamine hydrochloride is removed by filtration, the toluene layer is concentrated under reduced pressure to give 1.56 g a pale yellowish viscous oily material. The oily material is purified in the same manner as in Example 1 to give 1.21 g (yield: 62.1%) of O-ethyl S-n-propyl 2-phenylimino-3,4,5,6-tetrahydro-2H-1,3-thiazine-3-dithiophosphonate as colorless transparent liquid. $n_D^{25}$ = 1.5337.

The physical constants of the compounds provided in the above Examples and those of the compounds (I) prepared in the same manner as in Examples 1~3 are shown in the following Table 1.

TABLE 1

| Compd. No. | $R^1$ | $R^2$ | $R^3$ | $R^4$ | $R^5$ | $R^6$ | $R^7$ | X | | mp (°C.) | (temp. °C.) $n_D$ |
|---|---|---|---|---|---|---|---|---|---|---|---|
| 1 | EtO | EtO | H | H | H | H | H | S | colorless liquid | | (25)1.5713 |
| 2 | EtO | n-PrS | H | H | H | H | H | S | colorless liquid | | (25)1.5337 |
| 3 | EtO | i-PrNH | H | H | H | H | H | S | white crystals | 48.0~50.0 | |
| 4 | EtO | EtO | H | H | H | H | H | O | colorless liquid | | (25)1.5517 |
| 5 | EtO | n-PrS | H | H | H | H | H | O | colorless liquid | | (20)1.5877 |
| 6 | MeO | MeO | H | H | H | H | H | O | white crystals | 74.0~75.5 | |
| 7 | n-PrO | n-PrO | H | H | H | H | H | O | colorless liquid | | |
| 8 | EtO | MeNH | H | H | H | H | H | S | colorless liquid | | (20)1.5532 |
| 9 | EtO | i-BuS | H | H | H | H | H | O | colorless liquid | | (20)1.5786 |
| 10 | MeO | s-BuS | H | H | H | H | H | O | colorless liquid | | (20)1.5845 |
| 11 | EtO | s-BuS | H | H | H | H | H | O | colorless liquid | | (20)1.5811 |
| 12 | EtO | MeS | H | H | H | H | H | O | colorless liquid | | |
| 13 | EtO | i-PrNH | H | H | 2-Me | 4-Cl | H | S | white crystals | 77.0~78.5 | |
| 14 | EtO | n-PrS | H | H | 2-Me | 4-Cl | H | O | colorless liquid | | (25)1.5610 |
| 15 | EtO | n-PrS | H | H | 2-Me | 4-Cl | H | S | colorless liquid | | |
| 16 | EtO | i-BuS | H | H | 2-Me | 4-Cl | H | O | colorless liquid | | (20)1.5736 |

TABLE 1-continued

| Compd. No. | $R^1$ | $R^2$ | $R^3$ | $R^4$ | $R^5$ | $R^6$ | $R^7$ | X | | mp (°C.) | (temp. °C.) $n_D$ |
|---|---|---|---|---|---|---|---|---|---|---|---|
| 17 | EtO | MeS | H | H | 2-Me | 4-Cl | H | O | white crystals | 86.5~87.5 | |
| 18 | MeO | s-BuS | H | H | 2-Me | 4-Cl | H | O | colorless liquid | | (20)1.5854 |
| 19 | EtO | s-BuS | H | H | 2-Me | 4-Cl | H | O | colorless liquid | | (20)1.5775 |
| 20 | EtO | i-PrS | H | H | 2-Me | 4-Cl | H | O | colorless liquid | | (20)1.5773 |
| 21 | EtO | i-PrNH | H | H | 3-CF$_3$ | H | H | S | colorless liquid | | (25)1.5350 |
| 22 | EtO | EtO | Me | Me | H | H | H | O | white crystals | 33.0~34.5 | |
| 23 | EtO | n-PrS | Me | Me | H | H | H | O | white crystals | 37.5~39.0 | |
| 24 | EtO | i-BuS | Me | Me | H | H | H | O | white crystals | 40.5~42.0 | |
| 25 | MeO | s-BuS | Me | Me | H | H | H | O | white crystals | 41.0~42.5 | |
| 26 | EtO | n-BuS | Me | Me | H | H | H | O | pale yellowish liquid | | (20)1.5632 |
| 27 | EtO | C$_6$H$_5$S | Me | Me | H | H | H | O | colorless liquid | | (20)1.6009 |
| 28 | EtO | EtO | Me | Me | 2-MeO | H | H | O | pale brownish viscous liquid | | |
| 29 | EtO | n-PrS | Me | Me | 2-MeO | H | H | O | pale yellowish liquid | | |
| 30 | MeO | s-BuS | Me | Me | 2-MeO | H | H | O | pale yellowish liquid | | (20)1.5578 |
| 31 | EtO | s-BuS | Me | Me | 2-MeO | H | H | O | pale brownish liquid | | (20)1.5619 |
| 32 | EtO | n-PrS | H | H | 2-MeO | H | H | O | pale brownish viscous liquid | | |
| 33 | MeO | s-BuS | H | H | 2-MeO | H | H | O | pale brownish liquid | | |
| 34 | EtO | s-Bus | H | H | 2-MeO | H | H | O | white crystals | 45.0~46.5 | |
| 35 | EtO | n-PrS | Me | Me | 2-Me | 4-Cl | H | O | white crystals | 70.0~71.5 | |
| 36 | MeO | s-BuS | Me | Me | 2-Me | 4-Cl | H | O | white crystals | 48.5~49.5 | |
| 37 | EtO | n-BuS | Me | Me | 2-Me | 4-Cl | H | O | colorless liquid | | (20)1.5604 |
| 38 | EtO | EtO | Me | Me | 2-Me | 4-Cl | H | O | white crystals | 45.0~46.5 | |
| 39 | MeO | n-BuS | Me | Me | 2-Me | 4-Cl | H | O | colorless liquid | | (20)1.5574 |
| 40 | MeO | i-BuS | Me | Me | 2-Me | 4-Cl | H | O | yellow liquid | | (20)1.5631 |
| 41 | EtO | n-PrS | H | H | H | 4-n-Bu | H | O | colorless liquid | | (20)1.5639 |
| 42 | EtO | n-PrS | Me | Me | H | 4-n-Bu | H | O | colorless liquid | | (20)1.5549 |
| 43 | MeO | s-BuS | Me | Me | H | 4-n-Bu | H | O | pale yellowish liquid | | (20)1.5552 |
| 44 | EtO | s-BuS | Me | Me | H | 4-n-Bu | H | O | colorless liquid | | (20)1.5513 |
| 45 | EtO | n-BuS | Me | Me | H | 4-n-Bu | H | O | colorless liquid | | (20)1.5503 |
| 46 | EtO | n-PrS | H | H | 2-Me | 6-Me | H | O | white liquid | | (20)1.5728 |
| 47 | MeO | s-BuS | H | H | 2-Me | 6-Me | H | O | white liquid | | (20)1.5582 |
| 48 | EtO | n-BuS | H | H | 2-Me | 6-Me | H | O | white crystals | 50.0~51.5 | |
| 49 | CH≡CCH$_2$O | EtS | H | H | 2-Me | 6-Me | H | O | white crystals | 77.5~78.5 | |
| 50 | MeO | s-BuS | H | H | 2-i-Pr | H | H | O | colorless liquid | | |
| 51 | EtO | s-BuS | H | H | 2-i-Pr | H | H | O | colorless liquid | | (20)1.5626 |
| 52 | CH≡CCH$_2$O | EtS | H | H | 2-i-Pr | H | H | O | white crystals | 83.0~84.0 | |
| 53 | EtO | C$_6$H$_5$S | H | H | 2-i-Pr | H | H | O | colorless liquid | | (20)1.6004 |
| 54 | EtO | n-PrS | Me | Me | 2-i-Pr | H | H | O | white crystals | 50.5~52.0 | |
| 55 | MeO | s-BuS | Me | Me | 2-i-Pr | H | H | O | colorless liquid | | (20)1.5579 |
| 56 | EtO | s-BuS | Me | Me | 2-i-Pr | H | H | O | white crystals | 54.0~55.5 | |
| 57 | EtO | C$_6$H$_5$S | Me | Me | 2-i-Pr | H | H | O | colorless liquid | | (20)1.5883 |
| 58 | MeO | s-BuS | Me | Me | 2-Me | 6-Me | H | O | colorless viscous liquid | | (20)1.5542 |
| 59 | MeO | s-BuS | Me | Me | 2-Et | 6-Et | H | O | colorless viscous liquid | | (20)1.5507 |
| 60 | MeO | s-BuS | Me | Me | 2-i-Pr | 6-i-Pr | H | O | white crystals | 78.5~80.0 | |
| 61 | MeO | s-BuS | Me | Me | 2-Me | 4-Me | H | O | white viscous liquid | | (20)1.5603 |
| 62 | MeO | s-Bus | Me | Me | H | 4-EtO | H | O | pale yellowish viscous liquid | | (20)1.5736 |
| 63 | MeO | s-BuS | Me | Me | 2-F | 4-F | H | O | white crystals | 77.0~79.0 | |
| 64 | EtO | n-PrS | Me | Me | 2-F | 4-F | H | O | white crystals | 65.0~66.0 | |
| 65 | MeO | s-BuS | Me | Me | 2-Cl | 4-Me | H | O | colorless liquid | | (20)1.5680 |
| 66 | EtO | n-PrS | Me | Me | 2-Cl | 4-Me | H | O | white crystals | 51.5~53.5 | |
| 67 | EtO | EtO | Me | Me | 4-n-Bu | H | H | O | colorless transparent liquid | | |

Note
Me: methyl;
Et: ethyl;
Pr: propyl;
Bu: butyl

EXAMPLE 4

| | (Percent by weight) |
|---|---|
| Effective ingredient (Compound No. 25) | 2 |
| Clay | 88 |
| Talc | 10 |

The above components are mixed to give a powder.

EXAMPLE 5

| | (Percent by weight) |
|---|---|
| Effective ingredient (Compound No. 36) | 30 |
| Diatomaceous earth | 45 |
| White carbon | 20 |
| Sodium lauryl sulfate | 3 |
| Sodium lignin sulfate | 2 |

The above components are mixed to give a wettable powder.

EXAMPLE 6

| | (Percent by weight) |
|---|---|
| Effective ingredient (Compound No. 2) | 20 |
| Xylene | 60 |
| Polyoxyethylene phenylphenol polymer emulsifier | 20 |

The above components are mixed to give an emulsion.

REFERENTIAL EXAMPLE (Production of starting material)

A mixture of 18.0 g (0.068 mol) of N-4-n-butylphenyl-N'-3-hydroxypropylthiourea and 20 ml of 12N HCl is heated under reflux for 1 hour. After cooling, the mixture is basified with 100 ml of 4N NaOH and extracted with chloroform. The extract is dried and concentrated; and the resulting residue is recrystallized from hexane to give 14.7 g (yield: 88%) of 2-[(4-n-butylphenyl)imino]-3,4,5,6-tetrahydro-2H-1,3-thiazine, m.p. 77°~78.5° C.

The compounds (II) provided in the same manner as in the above Referential Example are shown in Table 2.

TABLE 2

| $R^3$ | $R^4$ | $R^5$ | $R^6$ | $R^7$ | mp (°C.) |
|---|---|---|---|---|---|
| H | H | H | H | H | 118–119 |
| Me | Me | H | H | H | 157–158 |
| H | H | 4-n-Bu | H | H | 77–78.5 |
| Me | Me | 4-n-Bu | H | H | 126–127 |
| H | H | 2-Me | 4-Cl | H | 133–134 |
| Me | Me | 2-Me | 4-Cl | H | 155.5–157 |
| H | H | 2-MeO | H | H | 126–129.5 |
| Me | Me | 2-MeO | H | H | 97–99 |
| H | H | 2-i-Pr | H | H | 151–152 |
| Me | Me | 2-i-Pr | H | H | 155–157 |
| H | H | 2-Me | 6-Me | H | 131–132 |
| Me | Me | 2-Me | 6-Me | H | 158–160 |
| H | H | 4-EtO | H | H | 128–130 |
| Me | Me | 2-Me | 4-Me | H | 135–138 |
| Me | Me | 2-i-Pr | 6-i-Pr | H | 199–200 |
| Me | Me | 2-Et | 6-Et | H | 132–133 |
| Me | Me | 2-F | 4-F | H | 169–171 |
| H | H | 3-$CF_3$ | H | H | 152–152.5 |
| Me | Me | 2-Cl | 4-Me | H | 145–147 |

(Note)
Me: methyl; Et: ethyl; Pr: propyl; Bu: butyl

EXPERIMENT 1

[Preparation of a test solution]

A solution of the compound (I) in a small amount of DMF (dimethylformamide) is diluted with distilled water containing TWEEN 20 (registered trademark) at a concentration of 100 ppm to prepare a predetermined amount of the test solution.

[Test Method]

A. Insecticidal test on larvae of *Spodoptera litura*

Cabbage leaves (5×5 cm) were soaked in the test solution and dried in air. Ten larvae (2 instar) of *Spodoptera litura* were put on the 2 cabbage leaves in a Petri dish (9 cm in diameter) and allowed to feed at 25° C. for 48 hours; and insecticidal rate was calculated.

B. Insecticidal test on larvae of *Plutella xylostella*

Cabbage leaves (5×5 cm) were soaked in the test solution and dried in air. Ten larvae (3 instar) of *Plutella xylostella* were put on the cabbage leaf in a Petri dish (9 cm in diameter) and allowed to feed at 25° C. for 48 hours; and insecticidal rate was calculated.

C. Insecticidal test on larvae of *Adoxophyes orana*

Tea leaves (whole leaves) were soaked in the test solution and dried in air. The three tea leaves were placed on a polyethylene cup (6 cm in diameter, 4 cm in depth). Ten larvae (4 instar) of *Adoxophyes orana* were put on the leaf in the cup and kept at 25° C. for 48 hours; and insecticidal rate was calculated.

D. Insecticidal test on susceptible adults of *Nephotettix cincticeps*

Stem of six to seven rice seedlings (1.5~2 leaves) were bundled up with a sponge tape, which was fixed in a polyethylene cup (6 cm in diameter, 4 cm in depth) containing a small amount of water.

Test solution (2 ml) was applied to the foliage of the plants in a rotary sprayer and the bunch was dried in air, and it was covered with a transparent plastic cylinder. Ten female adults to Nephotettix cincticeps were confined in the cylinder and allowed to feed at 25° C. for 48 hours. Then, insecticidal rate was calculated.

I. Insecticical test on susceptible larvae of *Myzus persicae*

J. Insecticidal test on resistant larvae of *Myzus persicae*

A leaf (3×3 cm) of a chinese cabbage was placed on a polyethylene cup (6 cm in diameter, 4 cm in depth) filled with 0.3% agar-gel. One apterous adult of *Myzus persicae* was put on the leaf and allowed to keep at 25° C. for 24 hours to make larviposition. After removal of the adult, 2 ml of the test solution was applied to the foliage under a rotary sprayer; and larvae of *Myzus persicae* were allowed to keep at 25° C. for 48 hours. Then insecticidal rate was calculated.

K. Miticidal test on adults of *Tetranychus cinnabarinus*

N. Miticidal test on adults *Tetranychus urticae*

A leaf (2 cm in diameter) of kidney beans was placed on a polyethylene cup (6 cm in diameter, 4 cm in depth) filled with 0.3% agar-gel. Twelve female adults were put on the leaf and allowed to keep at 25° C. for 24 hours. After removal of dead and unhealthy individuals, 2 ml of the test solution was applied to the leaf in a rotary sprayer. The adults were allowed to keep at 25° C. for 48 hours. Then insecticidal rate was calculated.

L. Miticidal test on larvae of *Tetranychus cinnabarinus*

O. Miticidal test on larvae of *Tetranychus urticae*

A leaf (2 cm in diameter) of kidney beans was placed on a polyethylene cup (6 cm in diameter, 4 cm in depth) filled with 0.3% agar-gel. Seven female adults were put on the leaf and allowed to keep at 25° C. for 24 hours to make them lay eggs.

After removal of the adults, 2 ml of the test solution was applied to the leaf in a rotary sprayer. The larvae was allowed to keep at 25° C. for 7 days and the number of dead hatched larvae out of all of those were counted; and miticidal rate was calculated.

M. Miticidal test on eggs of *Tetranychus cinnabarinus*

P. Miticidal test on eggs of *Tetranychus urticae*

The test was carried out in the same manner as in Tests L and O, the cup was kept at 25° C. for 7 days and the number of dead eggs were counted; and ovicidal rate was calculated.

Q. Insecticidal test on adults of *Epilachna vigintioctopunctata*

A leaf (6×6 cm) of an eggplant was soaked in the test solution and dried in air. Five imagos (per leaf) of *Epilachna vigintioctopunctata* was put on the leaf in a Petri dish (9 cm in diameter) and allowed to feed at 25° C. for 48 hours. Then insecticidal rate was calculated.

R. Insecticidal test on larvae of *Periplaneta americana*

A filter paper (9 cm in diameter) was soaked in the test solution in a Petri dish. Five larvae (1~7 days after hatching) were confined in the Petri dish and allowed to keep at 25° C. for 48 hours. Then insecticidal rate was calculated.

S. Insecticidal test on adults of *Callosobruchus chinensis*

Ten adults within 24 hours after adult eclosion was laid in a screw tube (1.8 cm in diameter, 5 cm in height) of which the top and the bottom were covered with stainless steel net. The adults in the screw tube were immersed in the test solution, dried in air, and allowed to keep at 25° C. for 48 hours. Then insecticidal rate was caluculated.

The results were shown in the following Table 3.

TABLE 3

| Comp No. | PPM | A | B | C | D | I | J | K | L | M | N | O | P | Q | R | S |
|---|---|---|---|---|---|---|---|---|---|---|---|---|---|---|---|---|
| 6 | 2000 | | | | | 87 | | 100 | 100 | | | | | | | |
| 4 | 2000 | | | | | 100 | | 100 | 100 | 93 | | | | | | |
|  | 1000 | | | | | 100 | | 100 | | 79 | 93 | | | | | |
|  | 250 | | | | | 100 | | 100 | | | | | | | | |
|  | 63 | | | | | 91 | | 95 | | | | | | | | |
|  | 16 | | | | | 87 | | 81 | | | | | | | | |
| 1 | 2000 | | | | | 100 | | 100 | | | | | | | 100 | |
|  | 1000 | | | | | 100 | 80 | 100 | | | | | | | | |
|  | 250 | | | | | 100 | | | | | | | | | 100 | |
|  | 63 | | | | | | | | | | | | | | 100 | |
| 22 | 2000 | | | | | 100 | | 100 | 100 | | | | | | | |
|  | 250 | | | | | 100 | 97 | 100 | 95 | | | | | | | |
|  | 63 | | | | | 100 | | | | | | | | | | |
|  | 16 | | | | | 96 | | | | | | | | | | |
| 7 | 2000 | | | | | 100 | | 100 | 100 | | | | | | | |
|  | 250 | | | | | 96 | | | | | | | | | | |
| 12 | 2000 | | | | | 74 | | | | | | | | | | |
| 17 | 2000 | | | | 71 | | | | | | | | | | | |
| 2 | 2000 | 100 | | | | 100 | | 100 | 90 | | | | | | 100 | |
|  | 1000 | 100 | | | | 100 | | | | | | | | | | |
|  | 250 | | | | | 100 | | | | | | | | | 100 | |
|  | 63 | | | | | | | | | | | | | | 70 | |
| 5 | 2000 | | | | | | | 100 | | | | | | | 100 | |
|  | 1000 | | | | | | | 77 | | | | | | | | |
| 15 | 2000 | 100 | | | | 100 | | 100 | | 83 | | | | | 100 | |
|  | 250 | | | | | 94 | | 97 | | | | | | | 100 | |
|  | 63 | | | | | | | | | | | | | | 100 | |
| 14 | 2000 | 100 | | | | 100 | | 100 | 100 | 83 | | | | | 100 | |
|  | 1000 | 100 | | 95 | | 100 | | 100 | | | 100 | | | | | |
|  | 250 | 70 | | 75 | | 81 | | 100 | | | 100 | | | | 100 | |
|  | 63 | | | | | | | 100 | | | 70 | | | | | |
|  | 16 | | | | | | | 95 | | | | | | | | |
| 23 | 2000 | 100 | | | | 100 | | 100 | 100 | | | | | | 100 | |
|  | 1000 | | | | | | | | | | 100 | | | | | |
|  | 250 | | | | | 100 | | 100 | 100 | | 97 | | | | 70 | |
|  | 63 | | | | | 100 | | 100 | 70 | | | | | | | |
|  | 16 | | | | | | | 87 | | | | | | | | |
| 20 | 2000 | 100 | | | | 100 | | 100 | | | | | | | | |
|  | 250 | 70 | | 100 | | | | 100 | | | | | | | | |
|  | 63 | | | 100 | | | | 95 | | | | | | | | |
| 10 | 2000 | | | | | 100 | | 100 | | | | | | | | |
| 18 | 2000 | 100 | | | | 100 | | 100 | 90 | | | | | | 100 | |
|  | 250 | | | | | | | 100 | | | | | | | | |
|  | 63 | | | | | | | 100 | | | | | | | | |
|  | 16 | | | | | | | 95 | | | | | | | | |
| 25 | 2000 | 100 | | | | 100 | | 100 | | 100 | | | | | 100 | |
|  | 1000 | | | | | | | 100 | | | 100 | | | | | |
|  | 250 | 100 | 75 | | | 100 | | 100 | | 97 | 100 | | | | 100 | |
|  | 63 | | | | | 100 | | 100 | 100 | 82 | 100 | | | | 100 | |
|  | 16 | | | | | | | 100 | | | | | | | | |
|  | 4 | | | | | | | 100 | | | | | | | | |
|  | 1 | | | | | | | 89 | | | | | | | | |
| 11 | 2000 | 100 | | | 75 | 100 | | 100 | 100 | | | | | | 100 | |
|  | 250 | | 90 | | | 100 | | 100 | | | 71 | | | | | |
|  | 63 | | | | | 100 | | 100 | | | | | | | | |
|  | 16 | | | | | | | 100 | | | | | | | | |
| 19 | 2000 | 100 | | | | 100 | | 100 | 100 | 82 | | | | | 100 | |
|  | 1000 | | | | | | | | | | 100 | | | | | |
|  | 250 | | | 85 | | 100 | | 100 | 90 | | 100 | | | | 100 | |
|  | 63 | | | | | 100 | | 100 | 90 | | | | | | 100 | |
|  | 16 | | | | | | | 100 | | | | | | | | |
| 9 | 2000 | 100 | | | | 100 | | 100 | 80 | | | | | | 100 | |
|  | 250 | | 70 | | | 100 | | 100 | | | 100 | | | | 100 | |
|  | 63 | | | | | 100 | | 100 | | | 92 | | | | | |
|  | 16 | | | | | 70 | | 95 | | | | | | | | |
| 16 | 2000 | 100 | | | | 100 | | 100 | | 70 | | | | | 100 | |
|  | 250 | | 70 | | | 100 | | 100 | 100 | | 100 | | | | 100 | |
|  | 63 | | | | | 100 | | 100 | | | 100 | | | | 80 | |
|  | 16 | | | | | 85 | | 100 | | | | | | | | |
|  | 4 | | | | | | | 71 | | | | | | | | |
| 24 | 2000 | 100 | | | 70 | 100 | | 100 | 100 | | | | | | 100 | |
|  | 1000 | | | | | | | | | | 100 | | | | | |
|  | 250 | | | | | 100 | | 100 | 100 | | 100 | | | | 100 | |
|  | 63 | | | | | 100 | | 100 | 90 | | 86 | | | | 70 | |
|  | 16 | | | | | | | 100 | | | | | | | | |
| 8 | 2000 | | | | 81 | 100 | | 100 | 100 | | | | | | | |

TABLE 3-continued

| Comp No. | PPM | A | B | C | D | I | J | K | L | M | N | O | P | Q | R | S |
|---|---|---|---|---|---|---|---|---|---|---|---|---|---|---|---|---|
| | 250 | | | | | | | 100 | | | | | | | | |
| 3 | 2000 | | | | | 100 | | 100 | | | | | | | | |
| | 1000 | | | | | 100 | | 97 | | | | | | | | |
| 13 | 2000 | | | | | 100 | | | | | | | | | 100 | |
| | 1000 | | | | | 100 | | | | | | | | | | |
| 21 | 2000 | | | | | | | 100 | | | | | | | | |
| 67 | 1000 | | | | | | | 100 | | | | | | | | 86 |
| | 250 | | | | | | | 90 | | | | | | | | |
| 32 | 1000 | | | | | | | 100 | | | | | | | | 76 |
| | 250 | | | | | | | 75 | | | | | | | | |
| 35 | 1000 | 100 | | | | 100 | | 100 | | 100 | | | | | 100 | 100 |
| | 250 | 75 | 85 | 100 | | 100 | | 100 | | 100 | 100 | 100 | 73 | | | 91 |
| | 63 | | | | | | | 100 | 100 | 94 | 100 | 80 | | | | 96 |
| | 16 | | | | | | | 100 | 100 | 74 | 98 | | | | | |
| | 1 | | | | | | | 100 | | | | | | | | |
| 42 | 1000 | 100 | | | | 100 | | 100 | 100 | | | | | | 100 | 100 |
| | 250 | | 70 | | | 100 | 82 | 100 | | | 74 | | | | | 84 |
| | 63 | | | | | 100 | | 100 | | | | | | | | 100 |
| | 16 | | | | | | | 94 | | | | | | | | 75 |
| 26 | 1000 | 75 | | | | 95 | | 100 | 95 | | | | | | 100 | 100 |
| | 250 | | | | | 100 | | 100 | | | 97 | | | | | 97 |
| | 63 | | | | | 73 | | 100 | | | | | | | | 100 |
| | 16 | | | | | | | | | | | | | | | 80 |
| 37 | 1000 | 95 | | | | 73 | | 100 | 90 | 73 | | | | | 70 | 100 |
| | 250 | | 80 | | | | | 100 | | | 100 | | | | | 100 |
| | 63 | | | | | | | 100 | 90 | | 90 | | | | | |
| | 16 | | | | | | | 100 | | | | | | | | |
| 45 | 1000 | 100 | | | | | | 100 | | | | | | | 100 | 100 |
| | 250 | | 85 | | | | | 100 | | | | | | | | 100 |
| | 63 | | | | | | | 76 | | | | | | | | 88 |
| 44 | 1000 | 100 | | | | 100 | | 100 | 100 | 81 | | | | | 100 | 100 |
| | 250 | | 80 | | | | | 100 | | | | | | | | 97 |
| | 63 | | | | | | | 100 | | | | | | | | 100 |
| | 16 | | | | | | | 89 | | | | | | | | 95 |
| 34 | 1000 | | | | | 100 | | 100 | 100 | | | | | | 100 | 91 |
| | 250 | | | | | | | 100 | | | | | | | | 94 |
| | 63 | | | | | | | 100 | | | | | | | | 81 |
| 33 | 1000 | 70 | | | | 100 | | 100 | 100 | | | | | | 100 | 90 |
| | 250 | | | | | 100 | | 100 | | | 97 | | | | | 86 |
| | 63 | | | | | 95 | | 100 | | | | | | | | 76 |
| | 16 | | | | | | | 91 | | | | | | | | |
| 36 | 1000 | 100 | | | 100 | 100 | | 100 | | 100 | | | | | 100 | 100 |
| | 250 | 85 | 95 | 90 | | 100 | 100 | 100 | | 100 | 100 | 100 | | | | 88 |
| | 63 | | 90 | | | 100 | | 100 | | 100 | 100 | 100 | | | 100 | 87 |
| | 16 | | | | | | | 100 | 100 | 79 | 100 | 100 | | | | 86 |
| | 1 | | | | | | | 100 | | | | | | | | |
| 43 | 1000 | 100 | | | | 100 | | 100 | 100 | 83 | | | | | 100 | 100 |
| | 250 | | 100 | | | 100 | 83 | 100 | | | 100 | | | | | 92 |
| | 63 | | | | | 100 | | 100 | 100 | | 85 | | | | | 93 |
| | 16 | | | | | | | 100 | | | | | | | | 92 |
| | 1 | | | | | | | 74 | | | | | | | | |
| 41 | 1000 | 95 | | | | | | 100 | 100 | | | | | | 100 | 100 |
| | 250 | | | | | | | 100 | | | 100 | | | | | 100 |
| | 63 | | | | | | | 100 | | | | | | | | 100 |
| | 16 | | | | | | | 94 | | | | | | | | 95 |
| 47 | 1000 | 100 | | | | 100 | | 100 | 100 | 94 | | | | | 100 | 100 |
| | 250 | 100 | | 70 | | 100 | 72 | 100 | | 100 | 100 | 100 | | 100 | | 100 |
| | 63 | 75 | | | | 100 | | 100 | | 100 | 100 | 80 | | 100 | 100 | 100 |
| | 16 | | | | | | | 100 | 100 | 91 | 92 | | | | | 86 |
| 46 | 1000 | 95 | | | | 71 | | 100 | 100 | | | | | | 100 | 100 |
| | 250 | 85 | | | | | | 100 | 100 | 91 | 100 | | | 80 | | 100 |
| | 63 | 70 | | | | | | 100 | 100 | | 85 | | | | 100 | 95 |
| | 16 | | | | | | | 100 | | | | | | | | 87 |
| 48 | 1000 | 100 | | | | | | 100 | 100 | | | | | | 100 | 100 |
| | 250 | 85 | | | | | | | | | | | | 100 | | 100 |
| | 63 | | | | | | | | | | | | | | | 100 |
| | 16 | | | | | | | | | | | | | | | 88 |
| 49 | 1000 | | | | | | | | | | | | | | | 79 |
| 50 | 1000 | 100 | | | | 82 | | 97 | 100 | 98 | | | | | 100 | 100 |
| | 250 | 75 | | | | | | 100 | 100 | 99 | 100 | 100 | | 100 | | 100 |
| | 63 | | | | | | | 100 | 100 | 83 | 100 | | | 80 | 90 | 94 |
| | 16 | | | | | | | 100 | 90 | | | | | | | 88 |
| | 4 | | | | | | | 89 | | | | | | | | |
| 54 | 1000 | 100 | | | | 100 | | 100 | 100 | | | | | | 80 | 100 |
| | 250 | | | | | 78 | | 100 | | | 85 | | | 100 | | 96 |
| | 63 | | | | | 81 | | 97 | 90 | | | | | | | 86 |
| | 16 | | | | | | | 70 | | | | | | | | 86 |
| 51 | 1000 | 100 | | | | 100 | | 100 | 100 | 92 | | | | | 100 | 100 |
| | 250 | | | | | 100 | 79 | 100 | | | 100 | | | 100 | | 100 |
| | 63 | | | | | 100 | | 100 | 100 | | | | | 80 | 100 | 100 |
| | 16 | | | | | | | 100 | | | | | | | 100 | 100 |

TABLE 3-continued

| Comp No. | PPM | A | B | C | D | I | J | K | L | M | N | O | P | Q | R | S |
|---|---|---|---|---|---|---|---|---|---|---|---|---|---|---|---|---|
| 52 | 1000 | | | | | | | | | | | | | | | 92 |
| | 250 | | | | | | | | | | | | | | | 100 |
| | 63 | | | | | | | | | | | | | | | 89 |
| 55 | 1000 | 100 | | | | 100 | | 100 | 100 | 86 | | | | | 100 | 100 |
| | 250 | 85 | | 70 | | 100 | | 100 | | | 100 | | | 100 | | 100 |
| | 63 | | | | | 100 | | 100 | 100 | 72 | 87 | | | 100 | 100 | 100 |
| | 16 | | | | | | | 97 | | | | | | | | 100 |
| 56 | 1000 | 95 | | | | 100 | | 100 | 100 | | | | | | 100 | 100 |
| | 250 | | | | | 100 | | 100 | | | | | | 100 | | 100 |
| | 63 | | | | | 100 | | 100 | | | | | | | | 100 |
| | 16 | | | | | | | 85 | | | | | | | | 100 |
| 57 | 1000 | | | | | | | | | | | | | | 100 | 90 |
| 39 | 1000 | 100 | | | | | | 100 | 100 | | | | | | 90 | 100 |
| | 250 | 80 | | | | | | 100 | 100 | | 100 | 100 | | | | 100 |
| | 63 | | | | | | | 100 | 100 | | 91 | | | | | 100 |
| | 16 | | | | | | | 86 | | | | | | | | |
| 40 | 1000 | 100 | | | | 100 | | 100 | 100 | 89 | | | | | 100 | 100 |
| | 250 | 70 | | | | 100 | | 100 | 100 | 87 | 100 | 100 | | | | 100 |
| | 63 | | | | | | | 100 | 100 | | 100 | 100 | | | | 100 |
| | 16 | | | | | | | 100 | 100 | 100 | | | | | | 100 |
| | 4 | | | | | | | 100 | | | | | | | | |
| | 1 | | | | | | | 83 | | | | | | | | |
| 61 | 1000 | 100 | | | | 97 | | 100 | 100 | | | | | | 100 | 100 |
| | 250 | 95 | 90 | | | | | | | | | | | | | |
| | 63 | | 80 | | | | | 100 | 95 | | | | | | | |
| | 16 | | | | | | | 100 | | | | | | | | |
| 47 | 1000 | 100 | | | | 100 | | 100 | 100 | 77 | | | | | 100 | 100 |
| | 250 | 100 | 100 | 95 | | 100 | | | | | | | | | 70 | 80 |
| | 63 | 75 | 100 | | | | | 100 | 100 | | | | | | | |
| | 16 | | 70 | | | | | 100 | | | | | | | | |
| 59 | 1000 | 100 | | | | 100 | | 100 | 100 | 98 | | | | | 100 | 100 |
| | 250 | 100 | 100 | | | 97 | | | | | | | | | | 90 |
| | 63 | | 100 | | | | | 100 | 100 | | | 70 | | | | |
| | 16 | | | | | | | 100 | 95 | | | | | | | |
| | 4 | | | | | | | 100 | | | | | | | | |
| 60 | 1000 | 100 | | | | 86 | | 100 | 100 | 96 | | | | | 100 | 100 |
| | 250 | 100 | 100 | | | | | | | | | | | | | 100 |
| | 63 | | 70 | | | | | 100 | 100 | | | | | | | 100 |
| | 16 | | | | | | | 100 | 100 | | | | | | | |
| | 4 | | | | | | | 100 | | | | | | | | |
| 62 | 1000 | 100 | | | | 100 | | 100 | 100 | | | | | | 100 | 100 |
| | 250 | 80 | | | | 79 | | | | | | | | | | |
| | 63 | | | | | | | 100 | | | | | | | | |
| | 16 | | | | | | | 95 | | | | | | | | |
| 64 | 1000 | 100 | | | | | | 100 | 100 | 97 | | | | | 100 | 100 |
| | 250 | 100 | 80 | 100 | | | | 100 | | 100 | 100 | 100 | | | | 90 |
| | 63 | | | 75 | | | | 100 | 100 | 91 | 100 | | | | 80 | |
| | 16 | | | | | | | 100 | | | 72 | | | | | |
| | 4 | | | | | | | 100 | | | | | | | | |
| 63 | 1000 | | | | 75 | 100 | | 100 | | | | | | | 100 | 100 |
| | 250 | | | | | 100 | | 100 | | 100 | 100 | 100 | | | | 100 |
| | 63 | | | | | 88 | | 100 | | 99 | 100 | 100 | | | 90 | 100 |
| | 16 | | | | | | | 100 | 100 | | 100 | | | | 70 | |
| | 4 | | | | | | | 100 | | | | | | | | |
| 66 | 1000 | 100 | | | | | | 100 | 100 | | | | | | 90 | |
| | 250 | | | | | | | 100 | 100 | | 100 | | | | | |
| | 63 | | | | | | | 100 | 80 | | | | | | | |
| 65 | 1000 | 100 | | | | 92 | | 100 | 100 | | | | | | 100 | 100 |
| | 250 | 75 | 95 | 80 | | | | 100 | | 100 | 100 | 70 | | | | 70 |
| | 63 | | 80 | | | | | 100 | | | 78 | | | | | |
| | 16 | | | | | | | 100 | 100 | | | | | | | |

(Note)
A, B, C, D, I, J, K, L, M, N, O, P, Q, R, and S represent the effects on insects or mites as described below.
A: *Spodoptera litura* (larvae)
B: *Plutella xylostella* (larvae)
C: *Adoxophyes orana* (larvae)
D: *Nephotettix cincticeps* (adults)
I: *Myzus persicae* (susceptible larvae)
J: *Myzus persicae* (resistant larvae)
K: *Tetranychus cinnabarinus* (adults)
L: *Tetranychus cinnabarinus* (larvae)
M: *Tetranychus cinnabarinus* (eggs)
N: *Tetranychus urticae* (adults)
O: *Tetranychus urticae* (larvae)
P: *Tetranychus urticae* (eggs)
Q: *Epilachna vigintioctopunctata* (adults)
R: *Periplaneta americana* (larvae)
S: *Callosobruchus chinensis* (adults)
The number means lethal rate (%).

As the result of the tests, it is found that the compounds of the present invention show potent effects on various kinds of harmful insects and mites, in particular

What we claim is:

1. A compound of the formula:

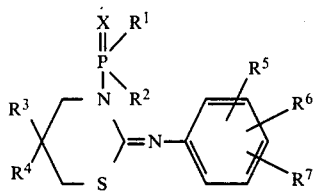

wherein $R^1$ and $R^2$ each is lower alkoxy, lower alkynyloxy, lower alkylthio, lower alkylamino, or $C_6$-$C_8$ arylthio selected from the group consisting of phenylthio, tolylthio and xylylthio; $R^3$ and $R^4$ each is hydrogen or lower alkyl; $R^5$, $R^6$, and $R^7$ each is hydrogen, lower alkyl, lower alkoxy, halogen, or trifluoromethyl; and X is oxygen or sulfur.

2. The compound claimed in claim 1, wherein $R^1$ and $R^2$ each is $C_1$-$C_6$ alkoxy, $C_2$-$C_5$ alkynyloxy, $C_1$-$C_6$ alkylthio, $C_1$-$C_6$ alkylamino, or $C_6$-$C_8$ arylthio selected from the group consisting of phenylthio, tolylthio and xylylthio; $R^3$ and $R^4$ each is hydrogen or $C_1$-$C_6$ alkyl; $R_5$ is $C_1$-$C_5$ alkyl, $C_1$-$C_6$ alkoxy, halogen, or trifluromethyl.

3. The compound claimed in claim 1, wherein X is oxygen.

4. The compound claimed in claim 1, wherein $R^1$ and $R^2$ each is $C_1$-$C_6$ alkoxy or $C_1$-$C_5$ alkylthio.

5. The compound claimed in claim 2, wherein X is oxygen.

6. The compound claimed in claim 2 wherein $R^1$ and $R^2$ each is $C_1$-$C_6$ alkoxy or $C_1$-$C_6$ alkylthio.

7. The compound claimed in claim 1, wherein the lower alkyl is selected from the group consisting of methyl, ethyl, propyl, isopropyl, butyl, isobutyl, sec-butyl, tert-butyl, pentyl, isopentyl, tert-pentyl, neo-pentyl, 1-methylbutyl, 1,2-dimethylpropyl and hexyl; the $C_1$-$C_6$ alkoxy is selected from the group consisting of methoxy, ethoxy, propoxy, isopropoxy, butoxy, pentyloxy and hexyloxy; and the $C_2$-$C_5$ alkynyloxy is selected from the group consisting of ethynyloxy, 2-propynyloxy, 3-butynyloxy, and 4-pentynyloxy.

8. The compound according to claim 2, wherein the $C_1$-$C_6$ alkylthio is selected from the group consisting of methylthio, ethylthio, propylthio, isopropylthio, butylthio, pentylthio and hexylthio and the $C_1$-$C_6$ alkylamino is selected from the group consisting of methylamino, ethylamino, propylamino, isopropylamino, butylamino, pentylamino and hexylamino.

9. An insecticidal composition comprising an insecticidally effective amount of one or more of the compounds of the formula:

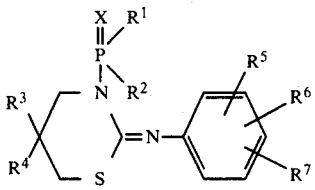

wherein $R^1$ and $R^2$ each is lower alkoxy, lower alkynyloxy, lower alkylthio, lower alkylamino, or $C_6$-$C_8$ arylthio selected from the group consisting of phenylthio, tolylthio and xylylthio; $R^3$ and $R^4$ each is hydrogen or lower alkyl; $R^5$, $R^6$, and $R^7$ each is hydrogen, lower alkyl, lower alkoxy, halogen, or trifluoromethyl; and X is oxygen or sulfur and one or more carriers therefor.

10. The composition according to claim 8, wherein the lower alkyl is selected from the group consisting of methyl, ethyl, propyl, isopropyl, butyl, isobutyl, sec-butyl, tert-butyl, pentyl, isopentyl, tert-pentyl, neo-pentyl, 1-methylbutyl, 1,2-dimethylpropyl and hexyl; the $C_1$-$C_6$ alkoxy is selected from the group consisting of methoxy, ethoxy, propoxy, isopropoxy, butoxy, pentyloxy and hexyloxy, and; the $C_2$-$C_5$ alkynyloxy is selected from the group consisting of ethynyloxy, 2-propynyloxy, 3-butynyloxy, and 4-pentynyloxy.

11. The composition according to claim 9, wherein the $C_1$-$C_6$ alkylthio is selected, from the group consisting of methylthio, ethylthio, propylthio, isopropylthio, butylthio, pentylthio and hexylthio.

12. The composition according to claim 9, having an effective insecticidal activity against insects belonging to the group consisting of Orthoptera, Hemiptera, Lepidoptera, Diptera, Coleoptera and mites.

13. The composition according to claim 9, which is in the form of a powder, granules, wettable powder, emulsion, suspension or aerosol.

14. The composition according to claim 13, which contains a solid carrier selected from the group consisting of vegetable powder, mineral powder and synthetic resin.

15. The composition according to claim 13, which contains a liquid carrier selected from the group consisting of hydrocarbons, alkanols, ethers, ketones, halogenohydrocarbons, esters, amides, nitriles, fats, oils, and water.

16. The composition according to claim 13, which contains an adjuvant selected from the group consisting of surface active agents, wetting agents, sticking agents, thickeners and stabilizers.

17. The composition according to claim 16, which contains an adjuvant selected from the group consisting of anionic surface active agents, nonionic surface active agents and water-soluble high-molecular compounds.

18. The composition according to claim 9, wherein said compound is present at a concentration of 0.1 to 99.9%.

19. The composition according to claim 18, wherein said compound is present at a concentration of 20 to 80%.

20. A method for treating insects comprising applying an insecticidally effective amount of the composition of claim 9 to insects or to the habitats of insects.

21. The method according to claim 20, wherein the application rate is 1-500 g/10 are.

* * * * *